United States Patent
Oikawa et al.

(10) Patent No.: US 8,879,868 B2
(45) Date of Patent: Nov. 4, 2014

(54) IMAGE PROCESSING METHOD FOR CONVERTING AN ANNUAL IMAGE

(75) Inventors: Satoshi Oikawa, Tochigi (JP); Michiaki Ohkubo, Tochigi (JP)

(73) Assignee: Honda Motor Co., Ltd., Tokyo (JP)

(*) Notice: Subject to any disclaimer, the term of this patent is extended or adjusted under 35 U.S.C. 154(b) by 0 days.

(21) Appl. No.: 13/565,314

(22) Filed: Aug. 2, 2012

(65) Prior Publication Data

US 2013/0089272 A1    Apr. 11, 2013

(30) Foreign Application Priority Data

Oct. 11, 2011 (JP) ................. 2011-224352

(51) Int. Cl.
- G06K 9/40 (2006.01)
- G01N 21/954 (2006.01)
- G06K 9/00 (2006.01)

(52) U.S. Cl.
CPC .................... *G01N 21/954* (2013.01)
USPC ......................................... 382/275; 382/190

(58) Field of Classification Search
USPC ......... 382/162, 164, 167, 173, 254, 275, 284, 382/285, 287, 294; 348/211.8, 222.1, 335, 348/345, 349–350
See application file for complete search history.

(56) References Cited

U.S. PATENT DOCUMENTS

| | | | | |
|---|---|---|---|---|
| 5,818,527 A | * | 10/1998 | Yamaguchi et al. | 348/335 |
| 6,670,991 B1 | * | 12/2003 | Takagi et al. | 348/349 |
| 7,483,590 B2 | * | 1/2009 | Nielsen et al. | 382/285 |
| 7,539,356 B2 | * | 5/2009 | Igari et al. | 382/284 |
| 8,131,113 B1 | * | 3/2012 | Jin | 382/284 |
| 2003/0197780 A1 | * | 10/2003 | Iwaki et al. | 348/36 |
| 2013/0089272 A1 | * | 4/2013 | Oikawa et al. | 382/275 |

FOREIGN PATENT DOCUMENTS

| | | |
|---|---|---|
| JP | 2000-331168 A | 11/2000 |
| JP | 2003-303342 | 10/2003 |
| JP | 2005-265489 | 9/2005 |

OTHER PUBLICATIONS

Japanese Office Action dated Sep. 2, 2014, 2 pages.
Chinese Office Action dated Jun. 16, 2014, with English Translation, 8 pages.

* cited by examiner

*Primary Examiner* — Amir Alavi
(74) *Attorney, Agent, or Firm* — Rankin, Hill & Clark LLP

(57) ABSTRACT

An image processing method includes a step of extracting an inner circle and an outer circle from an annular image, a step of obtaining the center for the extracted inner circle and the extracted outer circle respectively, and a step of moving a processing center serving as a reference in the polar coordinate conversion gradually between the center of the inner circle and the center of the outer circle to convert the circular image into a panoramic development image. According thereto, when an annular image of a side wall surface of a hole imaged by an omnidirectional imaging device (10) is converted into a panoramic development image according to a polar coordinate conversion, a distortion resulted from a position deviation occurred between an optical axis (L1) of the omnidirectional imaging device (10) and a central axis (L2) of the hole (H) can be corrected.

1 Claim, 5 Drawing Sheets

IMAGE PROCESSING METHOD FOR CONVERTING AN ANNUAL IMAGE

TECHNICAL FIELD

The present invention relates to an image processing method, particularly a correction method for converting an annular image into a panoramic development image.

BACKGROUND ART

Hitherto, the inspection of a defection, a detriment or the like on a side wall surface of a hole has been conducted on an image of the side wall surface photographed by an omnidirectional imaging device such as an endoscope or the like. Generally, the photographed annular image is converted into a panoramic development image for the inspection.

In the conversion, if the optical axis of the omnidirectional imaging device deviates from the central axis of the hole, it is necessary to conduct a correction process. As such correction process, there has been disclosed in Japanese Patent Laid-open No. 2000-331168 a technique which obtains the deviated amount between the optical axis of a video camera and the central axis of a tubular drain by conducting a data matching process as the video camera is used to photograph the inner surface of the tubular drain.

SUMMARY OF INVENTION

Technical Problem

However, in the technique disclosed in Japanese Patent Laid-open No. 2000-331168, it is necessary to prepare a reference image data as the video camera is preliminarily set to have the optical axis thereof matched with the central axis of the tubular drain. Therefore, when a variation is present in the same lot of products or at time of changing a lens, it is necessary to obtain a new reference image data. Moreover, it costs a long time to conduct the data matching process.

The present invention has been accomplished in view of the aforementioned problems, and it is therefore an object of the present invention to provide an image processing method capable of easily correcting a position deviation occurred between an optical axis and a central axis of a hole in converting a circular image into a panoramic development image without the necessity of preliminarily preparing a reference image data.

Solution to Problem

The present invention provides an image processing method for correcting a distortion resulted from a position deviation occurred between an optical axis of a omnidirectional imaging device and a central axis of a hole in converting an annular image of a side wall surface of the hole imaged by the omnidirectional imaging device into a panoramic development image according to a polar coordinate conversion. The image processing method of the present invention comprises steps of: extracting an inner circle and an outer circle from the annular image, obtaining the center for the extracted inner circle and the extracted outer circle respectively, and moving a processing center serving as a reference in the polar coordinate conversion gradually between the center of the inner circle and the center of the outer circle to convert the annular image into the panoramic development image.

According to the present invention, the annular image is converted into the panoramic development image while the processing center serving as a reference in the polar coordinate conversion is moved sequentially between the center of the inner circle and the center of the outer circle; thereby, the distortion resulted from the position deviation occurred between the optical axis of the omnidirectional imaging device and the central axis of the hole is corrected. Accordingly, it is possible to correct the distortion resulted from the position deviation on the basis of the annular image data itself.

Thereby, it is unnecessary to preliminarily prepare a correction data or obtain the reference image data when a variation is present in the same lot of products or at time of changing a lens as disclosed in Japanese Patent Laid-open No. 2000-331168. Accordingly, it is unnecessary to perform such a difficult operation as to install the omnidirectional imaging device in the hole without any position deviation. Further, without conducting such a time-consuming process as the data matching process or the like, it is possible to correct the distortion resulted from the position deviation'according to a simple processing. In the present invention, the hole includes a hole of a tube as well.

DESCRIPTION OF EMBODIMENTS

Figure 1:
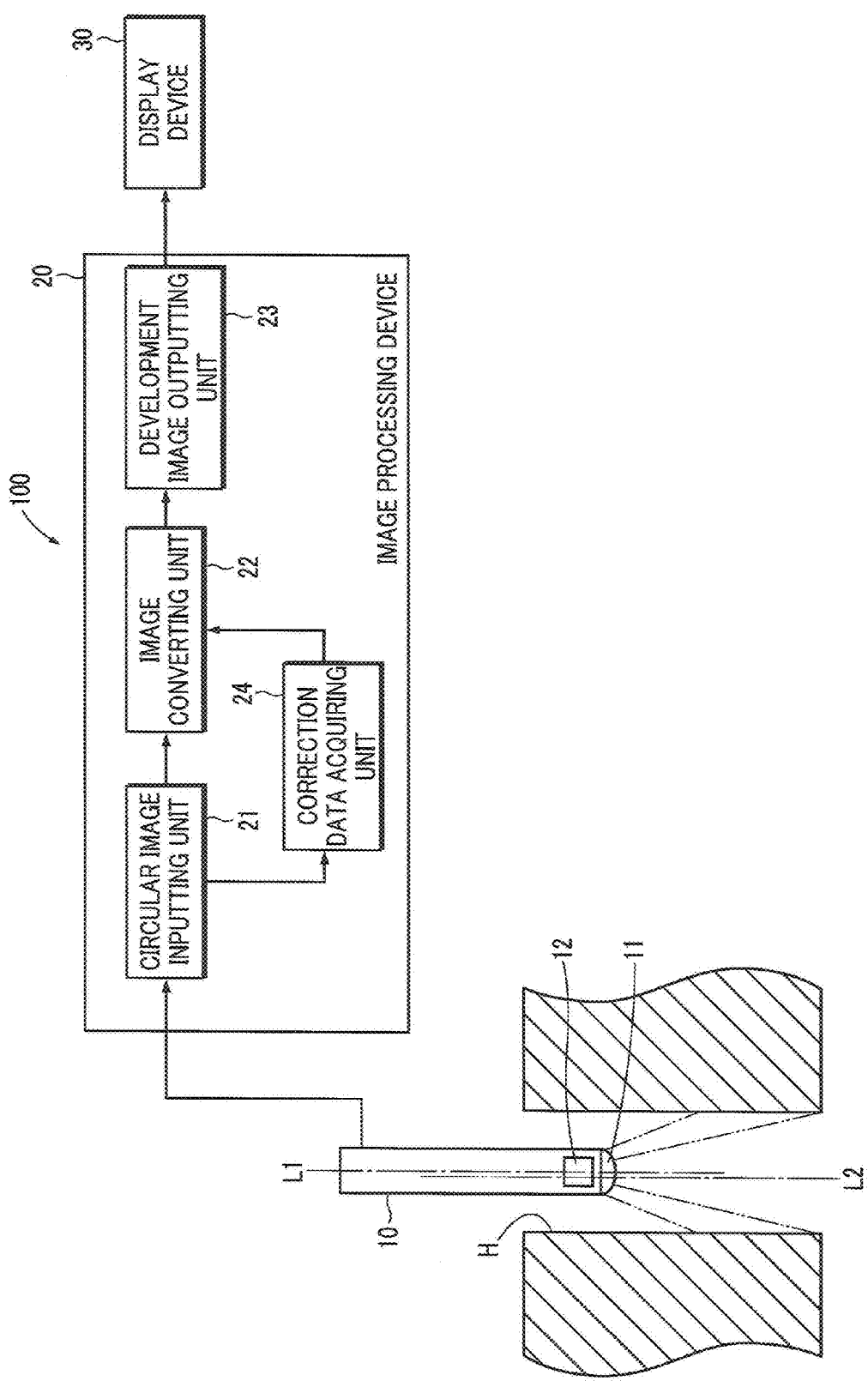
FIG. 1 is an explanatory diagram illustrating a side wall surface of a hole imaged by an omnidirectional imaging device according to an embodiment of the present invention.

Hereinafter, an embodiment of the present invention will be described with reference to the drawings. In the present embodiment, as illustrated in FIG. 1, the descriptions will be carried out on an example in which an omnidirectional imaging system 100 is used to photograph a photographing subject, namely a side wall surface of a hole H (hereinafter, referred to as the hole wall surface).

The hole H refers to a hole formed to dispose for example a fuel injection device (injector); however, the usage, the shape, the diameter, the depth or the like thereof is not limited. For example, it is acceptable that the hole H is a through hole or a hole having a bottom surface. Moreover, it is acceptable that the hole H is a straight hole having a constant diameter or a taper hole having a gradually varying diameter.

The omnidirectional imaging system 100 is composed of an omnidirectional imaging device 10, an image processing device 20 and a display device 30.

The omnidirectional imaging device 10 is configured to photograph the side wall surface of the hole H which is omnidirectional around 360 degrees into a circular image and output the circular image data. The omnidirectional imaging device 10 is provided with a wide angle lens 11 capable of imaging in 360 degrees (omnidirectional imaging lens), an image sensor 12 input with an incident light via the wide angle lens 11, and the like.

The wide angle lens 11 is disposed below a light receiving surface of the image sensor 12. Thereby, a circular image is formed on the light receiving surface of the image sensor 12 through the wide angle lens 11.

The image sensor 12 is composed of light receiving elements such as CCD, CMOS and the like arranged in two dimensions, and each light receiving element is configured to output a value in accordance with a received light mount. Therefore, the image sensor 12 generates a luminance distribution data having a plurality of received light amount values output from a plurality of light receiving elements. The circular luminance distribution data generated by the image sensor 12 is subjected to an A/D conversion and is output to the image processing device 20 as a circular image data.

The image processing device 20 is provided with a circular image inputting unit 21, an image converting unit 22, a development image outputting unit 23 and a correction data acquiring unit 24 as functional blocks thereof. The image processing device 20 is composed of a micro computer having a CPU, a ROM, a RAM, an image memory and the like.

The circular image data input from the omnidirectional imaging device 10 is imported into the image processing device 20 through the circular image inputting unit 21. The circular image data imported into the image processing device 20 is converted into the panoramic development image data in the image converting unit 22 and is output to the display device 30 through the development image outputting unit 23.

The panoramic development image displayed on the display device 30 is inspected visually by an inspector to discover whether or not a defect or the like is present on the hole wall surface. Although not drawn, it is also acceptable that the panoramic development image data is output to an analyzing device so as to have the analyzing device to automatically determine whether or not a defect or the like is present.

Figure 2:
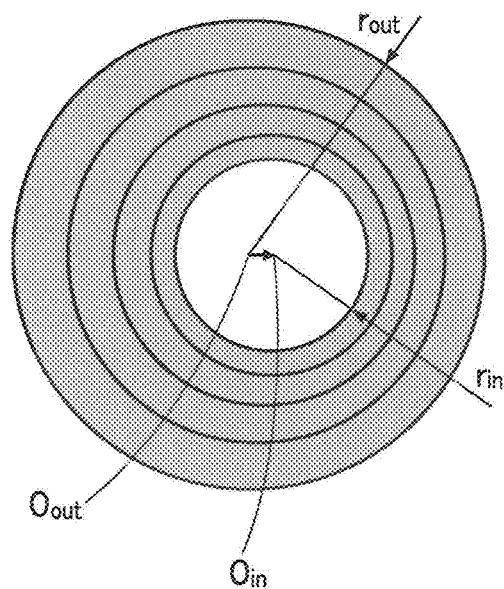
FIG. 2 is an explanatory diagram illustrating an annular image having a central position deviation.

However, as illustrated in FIG. 2, an annular region sandwiched by an outer circle and an inner circle is present in the circular image denoted by the circular image data output from the omnidirectional imaging device 10. Hereinafter, an image present in the region is called as an annular image.

The outer circle, which is the outer circumferential boundary of the circular image, denotes the upper opening of the hole H or the imaging limit of the omnidirectional imaging device 10. The inner circle denotes the lower end of the hole H having a circular shape in profile, such as the lower opening of the hole H, the bottom edges of the hole H, a corner section in the hole H or the like. Thus, even the hole H is not a through hole, it is possible to make present the inner circle. In addition, even a corner section is not present in the hole H, by managing the irradiation of lights, it is still possible to make present the inner circle.

The image converting unit 22 conducts a polar coordinate conversion on the annular image data sandwiched between the outer circle and the inner circle in the circular image data to generate the panoramic development image data. However, if the polar coordinate conversion is simply conducted on the annular image data in the image converting unit 22, the position deviation between the optical axis L1 of the omnidirectional imaging device 10 and the central axis L2 of the hole H (hereinafter, referred to as the central position deviation. Refer to FIG. 1), the vertical distortion of the wide angle lens 11 or the like will be reflected in the panoramic development image data.

Thus, the correction data acquiring unit 24 acquires the correction data for correcting the central position deviation, the vertical distortion or the like and outputs the acquired correction data to the image converting unit 22. The image converting unit 22 converts the annular image data into the panoramic development image data on the basis of the correction data.

If the central position deviation is not present, the center of the inner circle and the center of the outer circle are matched with each other in the annular image; thus, all the images photographed respectively for sections at the same height are concentric in the annular image, and as they are subjected to the polar coordinate conversion, the development images are linear in the horizontal direction.

Figure 3:
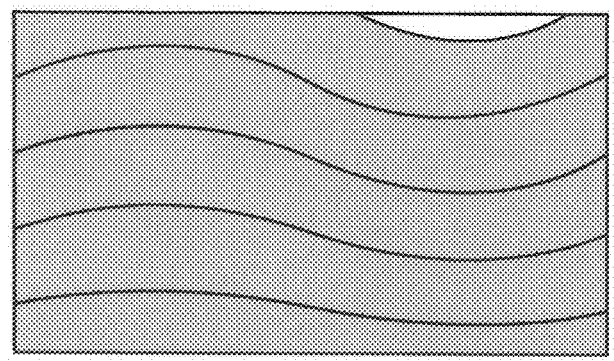
FIG. 3 is an explanatory diagram illustrating a panoramic development image having a central position deviation.

However, in actual the central position deviation is present. Therefore, if the annular image data is developed into the development images merely according to the polar coordinate conversion in the image converting unit 22, the images photographed respectively for sections at the same height are not actually linear but wave-like in the horizontal direction as illustrated in FIG. 3. Therefore, the correction data necessary for correcting the central position deviation is acquired by the correction data acquiring unit 24.

Figure 4:
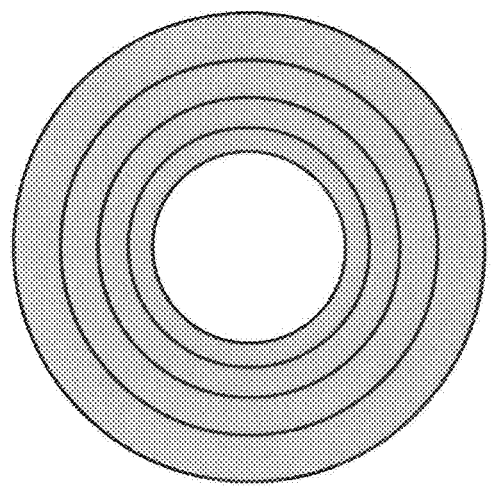
FIG. 4 is an explanatory diagram illustrating an annular image having a distortion in a lens in the vertical direction.

In an annular image photographed by a perfect wide angle lens 11 without any distortion, the images photographed for the hole wall surface with an equal interval in the height are concentric with the equal interval. However, in actual the vertical distortion is present in the lens 11; thereby, as illustrated in FIG. 4, the intervals between the concentric circles are not even. Therefore, if the annular image data is developed merely according to the polar coordinate conversion in the image converting unit 22, the development image is denoted by a panoramic image having intervals not corresponding to the actual intervals.

For example, if the wide angle lens 11 is a fish-eye lens, the distortion around the periphery of the image of a photographing subject is greater. There is a fish-eye lens of a stereographic projection type which increases the information amount of the periphery so as to alleviate the distortion.

If the fish-eye lens of a stereographic projection type is used as the wide angle lens 11 to photograph a photographing subject, the photographing subject will be photographed with a greater angle of field through the peripheral portion than through the central portion. Therefore, the photographing subject forms an image with a smaller angle of field when photographed through the central portion than through the peripheral portion. However, in the panoramic development image, it is desirable that the photographing subject is represented by the original dimensions in balance. Thus, the annular image data is developed according to the polar coordinate conversion by increasing sequentially the radius of a processing circle.

The correction data denoting specific ratios or the like for increasing the central distance between the processing circles or for increasing the radius of the processing circle is determined according to lens characteristics or the like of the wide angle lens 11 and is stored preliminarily in the RAM. Thus, the correction data acquiring unit 24 retrieves the correction data and output it to the image converting unit 22.

The display device 30 may be any common display device such as a liquid crystal display, an organic EL display, a CRT display or the like.

Figure 5:
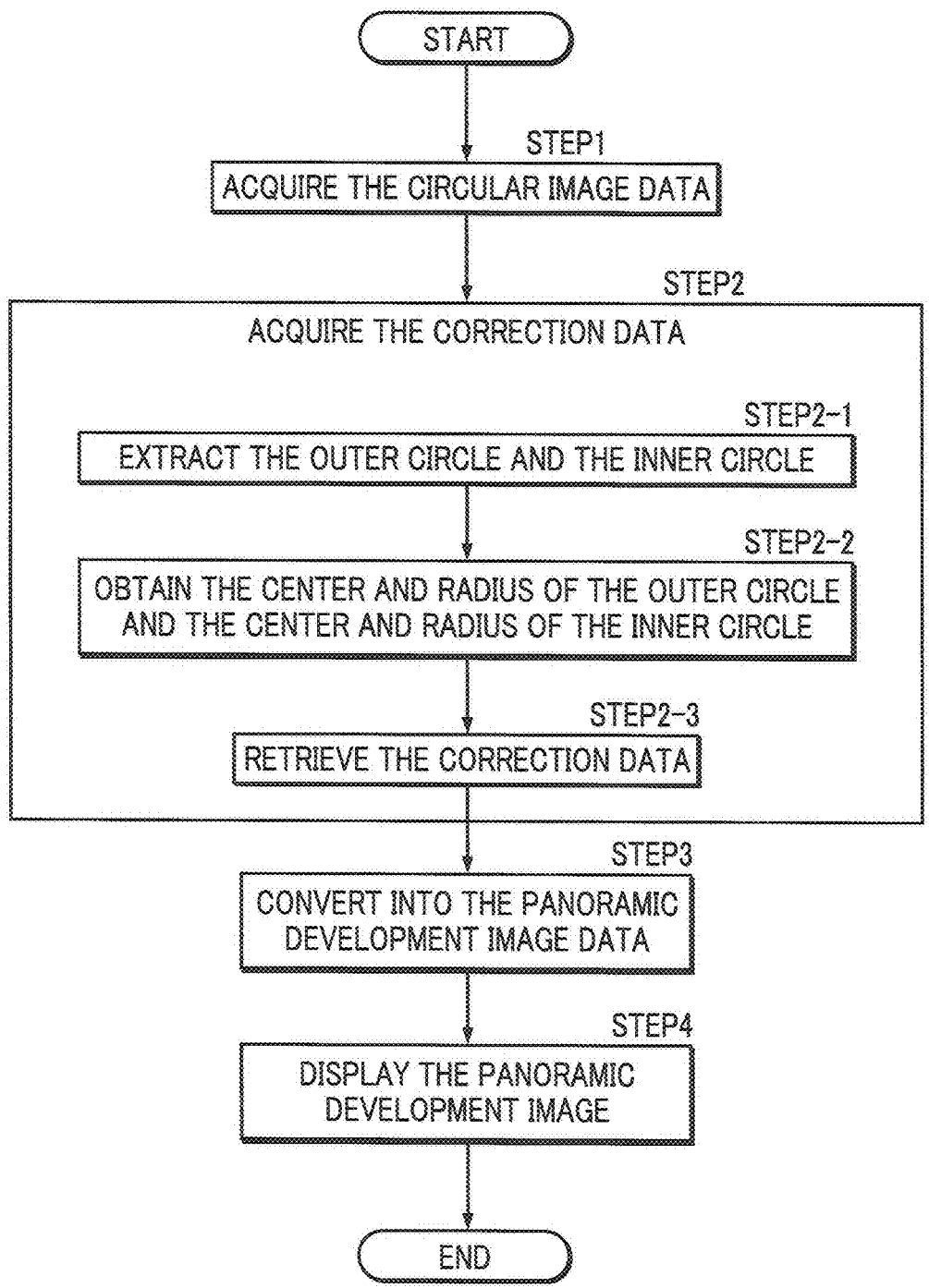
FIG. 5 is a flow chart illustrating a procedure conducted by an omnidirectional imaging system.

Hereinafter, the processing operations of the omnidirectional imaging system 100 will be described with reference to the flow chart in FIG. 5. Each process in the image processing device 20 is conducted according to a program stored preliminarily in the ROM.

Firstly, as illustrated in FIG. 1, an end portion of the omnidirectional imaging device 10 is inserted into the hole H to take an image. The circular image data acquired from the image photographed by the omnidirectional imaging device 10 is output to the circular image inputting unit 21 of the image processing device 20 (STEP 1). The circular image data input to the image processing device 20 is stored in the image memory.

Thereafter, the correction data acquiring unit 24 acquires the correction data and outputs the acquired correction data to the image converting unit 22 (STEP 2).

Specifically, the correction data acquiring unit 24 firstly conducts a common edge extracting process such as the binarization process or the like on the circular image data stored in the image memory to extract the outer circle and the inner circle illustrated in FIG. 2 (STEP 2-1).

Thereafter, the correction data acquiring unit 24 conducts a common computation process on the extracted outer circle and inner circle to obtain the center $O_{out}$ of the outer circle, the center $O_{in}$ of the inner circle, the radius $r_{out}$ of the outer circle and the radius $r_{in}$ of the inner circle respectively, and outputs the correction data including the aforementioned ones to the image converting unit 22 (STEP 2-2). The center $O_{out}$ of the outer circle corresponds to the optical axis L1 and the center $O_{in}$ of the inner circle corresponds to the central axis L2 of the hole H. The position deviation between the center $O_{out}$ of the outer circle and the center $O_{in}$ of the inner circle corresponds to the central position deviation.

Subsequently, the correction data acquiring unit 24 retrieves the correction data denoting the specific ratios or the like for increasing the central distance between the processing circles or for increasing the radius of the processing circle from the RAM and outputs the correction data to the image converting unit 22 (STEP 2-3).

Thus, the image converting unit 22 conducts the polar coordinate conversion to convert the annular image data into the panoramic development image data by using the correction data (STEP 3). Specifically, firstly, the image converting unit 22 sets the center $O_{in}$ of the inner circle as the development processing center (the center of a first processing circle) serving as the reference to start the development process.

Then, with the center $O_{in}$ of the inner circle serving as the center, the annular image data in the processing circle with the radius $r_{in}$ of the inner circle serving as the radius is subjected to the polar coordinate conversion for every angle determined according to the resolution or the like in the circumferential direction so as to be developed linearly in the horizontal direction. The calculated pixel position does not have to be in the same position as the minimum pixel of the annular image data. If the positions are not the same, the annular image data (luminance data) is subjected to an interpolation calculation at a ratio tangent to the calculated pixel position, and the image data (luminance data) may be obtained at the calculated pixel position.

Figure 6:
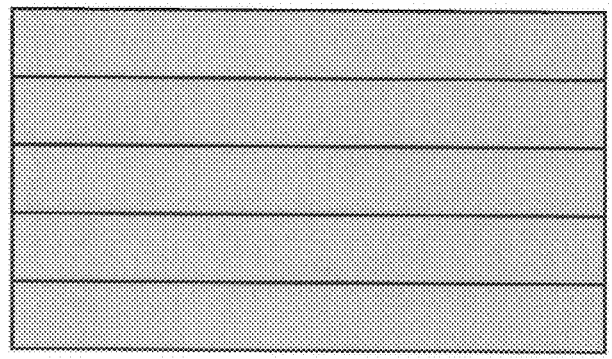
FIG. 6 is an explanatory diagram illustrating a panoramic development image after correction.

The development operation is repeated by moving sequentially the center of the processing circle from the center $O_{in}$ of the inner circle to the center $O_{out}$ of the outer circle linearly with an interval determined according to the resolution or the like (illustrated by the arrows in FIG. 2). Meanwhile, the radius of the processing circle is lengthened sequentially from the radius $r_{in}$ of the inner circle to the radius $r_{out}$ of the outer circle on the basis of the correction data for correcting the vertical distortion of the wide angle lens 11. Thereby, the annular image data is subjected to the polar coordinate conversion sequentially from the inner circle to the outer circle. Accordingly, as illustrated in FIG. 6, the development images which are linear in the horizontal direction are laminated sequentially to form a corrected panoramic development image.

Thereafter, the image processing device 20 outputs the obtained panoramic development image to the display device 30 through the development image outputting unit 23 (STEP 4). As a result thereof, the panoramic development image without any distortions can be displayed on the display device 30.

As described above, the correction data for correcting the central position deviation is acquired from the annular image data itself. Thereby, it is unnecessary to preliminarily prepare the correction data for correcting the central position deviation or to obtain a new correction data when a variation is present in the same lot of products or at time of changing the wide angle lens 11 as disclosed in Japanese Patent Laid-open No. 2000-331168. Accordingly, it is unnecessary to perform such a difficult and high accuracy operation as to insert the end portion of the omnidirectional imaging device 10 into the hole H without any central position deviation. Further, without conducting such a time-consuming process as the data matching process or the like, it is possible to obtain the panoramic development image with the central position deviation being corrected.

The embodiment of the present invention has been described in the above; however, the present invention is not limited thereto. For example, it has been described that the center of the processing circle is moved sequentially from the center $O_{in}$ of the inner circle to the center $O_{out}$ of the outer circle; it is also acceptable that the center of a processing circle is moved sequentially from the center $O_{out}$ of the outer circle to the center $O_{in}$ of the inner circle.

DESCRIPTION OF REFERENCE NUMERALS

10: omnidirectional imaging device; 11: wide angle lens; 12: image sensor; 20: image processing device; 21: circular image inputting unit; 22: image converting unit; 23: development image outputting unit; 24: correction data acquiring unit; 30: display device; 100: omnidirectional imaging system; H: hole; L1: optical axis of omnidirectional imaging device; L2: central axis of hole

The invention claimed is:
1. An image processing method for correcting a distortion resulted from a position deviation occurred between an optical axis of an omnidirectional imaging device having a wide angle lens, and a central axis of a hole in converting an annular image of a side wall surface of the hole imaged by the omnidirectional imaging device into a panoramic development image according to a polar coordinate conversion, the method comprising:
   extracting an inner circle and an outer circle from the annular image, wherein the outer circle comprises an outer circumferential boundary of the annular image and denotes an upper opening of the hole or an imaging limit of the omnidirectional image device, and the inner circle denotes a lower end of the hole having a circular shape in profile;
   obtaining first correction data including the center for the extracted inner circle and the extracted outer circle respectively; and
   moving sequentially a processing center serving as a reference in the polar coordinate conversion between the center of the inner circle and the center of the outer circle based on the first correction data, while adjusting sequentially a radius of a processing circle between a radius of the inner circle and a radius of the outer circle based on second correction data for correcting a vertical distortion of the wide angle lens to convert the annular image into the panoramic development image.

* * * * *